United States Patent
Lin et al.

(10) Patent No.: US 8,614,078 B2
(45) Date of Patent: Dec. 24, 2013

(54) CONTAMINANT REDUCING AMIDE FUNCTIONALIZED ORDERED MESOPOROUS CARBON COMPOSITION

(75) Inventors: Chung-Ho Lin, Columbia, MO (US); Brian Thompson, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 13/448,065

(22) Filed: Apr. 16, 2012

(65) Prior Publication Data

US 2013/0280781 A1    Oct. 24, 2013

Related U.S. Application Data

(60) Provisional application No. 61/517,189, filed on Apr. 15, 2011.

(51) Int. Cl.
*C12N 11/02*    (2006.01)
(52) U.S. Cl.
USPC .......................................................... 435/177
(58) Field of Classification Search
USPC ........................... 435/177; 427/402; 536/23.2
See application file for complete search history.

(56) References Cited

U.S. PATENT DOCUMENTS 8,246,999 B2 *    8/2012    Lin et al. ....................... 424/502
2007/0248760 A1 *    10/2007    Chmelka et al. .............. 427/402

OTHER PUBLICATIONS

Hartmann M. Ordered Mesoporous Materials for Bioadsorption and Biocatalysis. Chemistry of Materials 17:4577-4593, 2005.*
Taguchi A. et al. Ordered Mesoporous Materials in Catalysis. Microporous and Mesoporous Materials 77:1-45, 2005, avaliable Oct. 30, 2004.*
Gu Z. et al. Synthesis and Evaluation of Iron Containing Ordered Mesoporous Carbon for Arsenic Adsorption. Microporous and Mesoporous Materials 102:265-273, 2007, available Jan. 18, 2007.*

* cited by examiner

Primary Examiner — Ralph Gitomer
(74) Attorney, Agent, or Firm — Polsinelli PC

(57) ABSTRACT

The present invention is directed to compositions and methods related to delivering degradative enzymes to remove/remedy environmental pollutants. The inventive material comprises a series of amide-functionalized ordered mesoporous carbon (AFOMC), which utilizes chemical conjugation techniques for the tethering of enzymes to the surface of the synthesized AFOMC. The delivery mechanism may be utilized to express a wide variety of toxin-degrading enzymes for removal/remediation of organic pollutants.

4 Claims, 12 Drawing Sheets

SEQUENCE LISTING

```
<160> NUMBER OF SEQ ID NOS: 8

<210> SEQ ID NO 1
<211> LENGTH: 34
<212> TYPE: DNA
<213> ORGANISM: Escherichia coli
<220> FEATURE:
<221> NAME/KEY: misc_feature
<223> OTHER INFORMATION: PCR Primers, without 6x His 5' AtzA

<400> SEQUENCE: 1
aggaggtaga tacatgcaaa cactcagcat ccag                              34

<210> SEQ ID NO 2
<211> LENGTH: 45
<212> TYPE: DNA
<213> ORGANISM: Escherichia coli
<220> FEATURE:
<221> NAME/KEY: misc_feature
<223> OTHER INFORMATION: PCR Primers, without 6xHis, 3' AtzA

<400> SEQUENCE: 2
ggggttatgc tatcactatt attactagag gctgcgccaa gctgg                  45

<210> SEQ ID NO 3
<211> LENGTH: 42
<212> TYPE: DNA
<213> ORGANISM: Escherichia coli
```

```
<220> FEATURE:
<221> NAME/KEY: misc_feature
<223> OTHER INFORMATION: PCR Primers, without 6xHis, T7 Promoter

<400> SEQUENCE: 3
atattaatac gactcactat agggagataa ggaggtagat ac                     42

<210> SEQ ID NO 4
<211> LENGTH: 50
<212> TYPE: DNA
<213> ORGANISM: Escherichia coli
<220> FEATURE:
<221> NAME/KEY: misc_feature
<223> OTHER INFORMATION: PCR Primers, without 6xHis, T7 Terminator

<400> SEQUENCE: 4
atatcaaaaa acccctcaag acccgtttag aggccccaag gggttatgct             50

<210> SEQ ID NO 5
<211> LENGTH: 50
<212> TYPE: DNA
<213> ORGANISM: Escherichia coli
<220> FEATURE:
<221> NAME/KEY: misc_feature
<223> OTHER INFORMATION: PCR Primers, with 6xHis, 5' His AtzA

<400> SEQUENCE: 5
aggaggtaga tacatgcatc accatcacca tcaccaaacg ctcagcatcc             50

<210> SEQ ID NO 6
<211> LENGTH: 45
<212> TYPE: DNA
<213> ORGANISM: Escherichia coli
<220> FEATURE:
<221> NAME/KEY: misc_feature
<223> OTHER INFORMATION: PCR Primers, with 6xHis, 3' AtzA

<400> SEQUENCE: 6
ggggttatgc tatcactatt attactagag gctgcgccaa gctgg                  45

<210> SEQ ID NO 7
<211> LENGTH: 43
<212> TYPE: DNA
<213> ORGANISM: Escherichia coli
<220> FEATURE:
<221> NAME/KEY: misc_feature
<223> OTHER INFORMATION: PCR Primers, with 6xHis, T7 Promoter

<400> SEQUENCE: 7
atattaatac gtactcacta tagggagata aggaggtaga tac                    43

<210> SEQ ID NO 8
<211> LENGTH: 50
<212> TYPE: DNA
<213> ORGANISM: Escherichia coli
<220> FEATURE:
<221> NAME/KEY: misc_feature
<223> OTHER INFORMATION: PCR Primers, with 6xHis, T7 Terminator

<400> SEQUENCE: 8
atatcaaaaa acccctcaag acccgtttag aggccccaag gggttatgct             50
```

CONTAMINANT REDUCING AMIDE FUNCTIONALIZED ORDERED MESOPOROUS CARBON COMPOSITION

RELATED APPLICATIONS

The present application claims priority to U.S. Provisional Application No. 61/517,189, filed on Apr. 15, 2011 the teachings and contents of which are incorporated herein by reference.

SEQUENCE LISTING

This application contains a sequence listing in computer readable format, the teachings and content of which are hereby incorporated by reference.

FIELD OF INVENTION

The present invention relates to compounds and methods for remediation of environmental pollutants, more specifically, to a series of amide-functionalized ordered mesoporous carbon for delivery of toxin-degrading enzymes for removal/remediation of organic pollutants.

BACKGROUND OF INVENTION

Atrazine (ATR, 2-chloro-4-(ethylamino)-6-(isopropylamino)-1,3,5-triazine) has been one of the most widely applied herbicides in the US and Midwestern states. An estimated 36.3 million kg of ATR is applied annually to more than 69% of all U.S. corn acreage (United States Department of Agriculture, 2004). The contamination of surface and ground water by ATR and its chlorinated metabolites has raised public health and ecological concerns recently due to their endocrine disruption activities and potential risk of gastroschisis (Hayes et al., 2006; Waller et al., 2010). The ATR and its metabolites are persistent in the environmental and the mineralization of ATR and its chlorinated metabolites or complete cleavage of the triazine ring in the environment is limited to less than 2-10%. A 2006 study by the U.S. Geological Survey found ATR and its metabolites were detected in approximately 75 percent of stream water and about 40 percent of all groundwater samples from agricultural areas tested between 1992 and 2001 (Gilliom et al., 2006).

Despite the persistence of ATR and its metabolites in the VBS environment (Lin et al., 2005), the enzymes including chlorohydrolase AtzA produced by naturally occurring degradative bacteria *Pseudomonas* sp. strain ADP rapidly hydrolyzes the atrazine to the much less toxic and less mobile metabolite hydroxyatrazine. The catabolic genes that encode for the enzymes responsible for each step in the ATR degradation process have been well characterized (FIG. 1). *Pseudomonas* sp. strain ADP can utilize ATR and its metabolites as a carbon source and sole nitrogen source (Mandelbaum et al., 1995; Martinez et al., 2001). This property is due to the presence of the pADP-1 plasmid, a 108-kDA catabolic plasmid which encodes for all the metabolic enzymes necessary to completely degrade ATR to $CO_2$ and $NH_3$ (De Souza et al., 1998a; Martinez et al., 2001). The AtzA-C enzymes are not unique to *Pseudomonas* sp. strain ADP, but are found among soil bacteria isolates across the U.S. and Europe (De Souza et al., 1998b). The atzA chlorohydrolase metalloenzyme not only has the ability to dechlorinate atrazine into the significantly less toxic hydroxyatrazine, but also shows degradative activity to other s-triazines, such as simazine and desethylatrazine (Boundy-Mills et al., 1997; De Souza et al., 1996). Catabolic gene atzB metabolizes hydroxyatrazine to N-isopropylammelide, whose hydrolytic deamidation to cyanuric acid and isopropylamine is catalyzed by atzC (Boundy-Mills et al., 1997; Sadowsky et al., 1998). Gene atzD encodes a cyanuric acid amidohydrolase, which converts cyanuric acid to biuret. The presence of the atzDEF operon is unique to *Pseudomonas* sp. strain ADP and allows this bacterium to further catabolize the cyanuric acid (produced by the activities of AtzA-C) into $CO_2$ and $NH_3$ (Martinez et al., 2001). Biuret hydrolase is encoded by atzE and allophanate hydrolase is encoded by atzF, resulting in the conversion of biuret to allophanate and allophanate to $CO_2$ and $NH_3$ (Martinez et al., 2001). This plasmid is highly transmittable between microorganisms, and the expression of these genes, particularly atzD and F, are sensitive to alternative N sources in the environment (atz+ to atz−) (Garcia-Gonzalez et al., 2003). The purification and optimization of ATR enzymes for large scale remediation of organic pesticides including atrazine were first commercialized by CSIRO Enzyme Based Bioremediation Technology. However, the persistence of the enzymes such as AtzN has short life under the field conditions. The enzymatic activities cannot be sustained more than 8-10 days.

The recent success of enzyme conjugation technology and ordered mesoporous material synthesis (Hartmann, 2005) has allowed the encapsulation of enzymes and other biomolecules into ordered mesoporous material. According to IUPAC definition, material containing pores with diameters ranging from 2 to 50 nm are classified as ordered mesoporous material. The modified ordered mesoporous carbon material have high specific surface area, large specific pore volume, regular arrays of uniform nanopores, and narrow pore size of distribution which provide a large adsorption capacities and unique temples for functional modification. To immobilize the bioactive biomolecules or enzymes on the surface of the ordered mesoporous material, the surface of porous materials usually needs to be modified and functionalized. The functionalization of the materials usually carries out by reacting with organic or inorganic oxidative agents, such as nitric acid, ozone, or ammonium persulfate, followed by the substitution of oxidative groups by functionalities containing amine (—$NH_2$), thiol (R—SH) or free sulfhydryl (—SH) (Contescu, 1998; Hartmann, 2005; Jarrais, 2005; Puri, 1971; Tamai, 2006a). The functionalization processes provide the functional groups required for conjugation of biomolecules or enzymes. Hypothetically, the ordered mesoporous materials immobilized with bioactive enzymes or biomolecules should not only retain their functional enzymatic or biological characteristics by the enzymes/biomolecules immobilized on the surface, but also exhibit high specific surface areas and large adsorption capacities for the organic pollutants, like atrazine, through electrostatic interactions and/or covalent bindings.

Therefore, there is a need to provide a new and improved series of enzymatic delivery compounds with improved surface specificity and adsorption capacity and the ability to retain the enzymes' biological characteristics during delivery.

SUMMARY OF INVENTION

The present invention provides a new and improved series of amide-functionalized ordered mesoporous carbon (AFOMC) as a vehicle and system to deliver enzymes that degrade pollutants or toxins. The system is suitable for the production and delivery of materials such as bioparticles, proteins and small molecules. Preferably, the AFOMC of the present invention utilize atrazine-degrading enzymes, including but not limited to AtzA, AtzB, AtzC, AtzD, AtzE, AtzF, and combinations of these enzymes. The AFOMC of the present invention have a variety of applications, including, but not limited to, a biofilter, a kit for removing pollutants or toxins, biocatalysts, fuel cells, imaging, biofuel production, and biosensors. A method for removing pollutants or toxins from water and soil sources is also disclosed. The method includes the steps of introducing the AFOMC into a water or soil source and allowing the AFOMC to enhance both adoption and degradation of pollutants and, optionally, to allow the tethered enzymes to persist over time. The present invention utilizes chemical conjugation techniques for the tethering of enzymes to the surface of the synthesized AFOMC. The delivery mechanism may be utilized to express a wide variety of toxin-degrading enzymes for removal/remediation of the organic pollutants. In addition, this conjugation of bioactive enzymes onto the amide-functionalized ordered mesoporous carbon have a wide range of other commercial applications ranging from development of biocatalysts, biofilters, fuel cells, drug delivery systems, other medical therapeutics and bio sensors.

DEFINITIONS

"Pollutants" and "Toxins", for purposes of the present invention, include any undesirable substance found within a material or liquid. A pollutant or toxin may be found in air, gas, liquid, gel, soil, plants, food materials, water sources, and combinations thereof. This list is not meant to be limiting, as any undesirable element found in a source could be used for purposes of the present invention.

"MOI" for purposes of the present invention means molecules of interest. The molecules of interest is preferably an enzyme, but is not limited and can include bioparticles, proteins, or small molecules. Any material useful in being conjugated and immobilized to the AFOMC can be used for purposes of the present invention and is included in the definition of MOI.

DETAILED DESCRIPTION OF INVENTION

Figure 1:
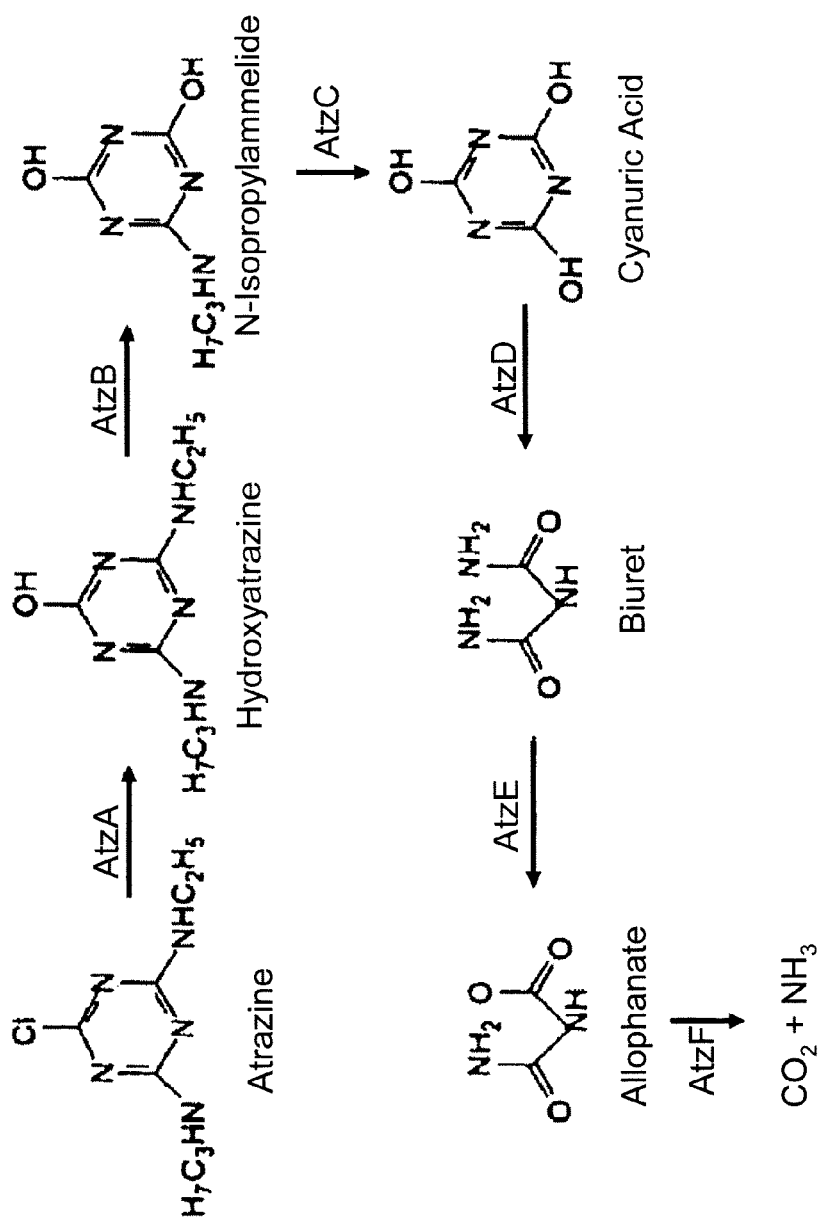
FIG. 1 illustrates the catabolic degradation of atrazine by P. ADP (Martinez et al., 2001).

The present invention provides for compositions and method of use for amide-functionalized ordered mesoporous carbon (AFOMC) as a vehicle to deliver material of interest ("MOT") to a preferred material or target. Preferably, the MOT are enzymes that degrade pollutants or toxins to aide in remediation and cleaning of the material or target. The AFOMC of the present invention comprise at least one MOI conjugated to the AFOMC. Preferably, the AFOMC of the present invention comprise at least one enzyme conjugated to the AFOMC capable of removing a pollutant or toxin from a source.

A method for creating the AFOMC of the present invention is also provided. The method comprises the steps of synthesis of an ordered mesoporus carbon, purifying the MOI, and conjugating and immobilizing the MOI to the surface of the AFOMC whereby allowing the AFOMC to then be delivered to a material or target. In a preferred embodiment, the method of making the AFOMC of the present invention include the steps of synthesis of an ordered mesoporus carbon, producing and purifying the target enzyme, and conjugating and immobilizing the enzyme on the ordered mesoporus carbon. Preferably, the method comprises the steps of chemically modifying the amine residues on the AFOMC via use of SHTH to chemically conjugate biotin in its binding pockets; chemically conjugating to neutravidin via the C6 SFB chemistry; using purified enzyme to chemically conjugate to nuetravidin via the C6 SFB chemistry; and binding the biotinylated AFOMC to the nuetravidinated purified enzyme.

A method of creating a filter or biofilter and the resultant product is also provided by the present invention. The biofilter preferably comprises a porous material and the AFOMC of the present invention. Preferably, the MOI bound to the AFOMC are exposed to the material being guided through the biofilter, such that pollutants and toxins are removed from the material being guided through the biofilter as it passes. Preferably, the material being guided through the biofilter is a liquid, more preferably, the liquid is water. However, any material capable of passing through a filter that may benefit from the removal of pollutants or toxins will work for purposes of the present invention.

Any MOI that is beneficial in removing pollutants or toxins from a material will work for purposes of the present invention. Preferably, the MOI is an enzyme. Any enzymes that break down pollutants or toxins will work for purposes of the present invention. One preferred class of enzymes are atrazine-degrading enzymes. Atrazine-degrading enzymes preferably include, but are not limited to AtzA, AtzB, AtzC, AtzD, AtzE, AtzF, and combinations thereof. Another preferred class of enzymes are hydrolase enzymes. Hydrolase enzymes include, but are not limited to esterases, sugar hydrolases, ether bond hydrolases, proteases, carbon-nitrogen non-peptide hydrolases, acid anhydride hydrolases, carbon-carbon hydrolases, and combinations thereof. In a preferred embodiment, the hydrolase is a sugar hydrolases, and more preferably it is β-galactosidase. Additionally preferred MOIs include, but are not limited to Xp1A cytochrome for removing RDX, PnrA for removing TNT, DfbB dioxin dioxenase for removing dioxin, ChRchromium reductase for reducing chromium 6+ to chromium 3+, and the like.

The AFOMC of the present invention can be used for air pollution, water pollution, soil contamination, and radioactive pollution. Preferably, the present invention can be used to aid in air pollution, such as, but not limited to, acid rain, air quality, chlorofluorocarbon, smog, and particulates. With regard to water pollution, the present invention can help remove pollutants and toxins to help with, but not limited to, the environmental impact of pharmaceuticals and personal care products in the water system, environmental monitoring of pollutants, eutrophication, hypoxia, marine debris, marine pollution, ocean acidification, oil spills, thermal pollutions, urban runoff, waste water, water quality, and waterborne disease. Soil contamination that can be helped using the present invention includes, but is not limited to bioremediation, phytoremediation, herbicides, pesticides, and soil guideline values. Some exemplary pollutants that can be removed using the present invention include, but are not limited to, atrazine, ortho-nitrophenyl-β-galactosidase (ONPG), chlorinated hydrocarbons, heavy metals, chromium, cadmium, lead, methyl tert-butyl ether (MTBE), zinc, arsenic, benzene, petrochemicals, carbon dioxide, greenhouse gases, and the like.

In a preferred embodiment, the AFOMC of the present invention remove at least 20% of the pollutants or toxins in the material exposed to the AFOMC, more preferably at least 30% are removed, still more preferably at least 40% are removed, more preferably, at least 50% are removed, still more preferably at least 60% are removed, more preferably at least 70% are removed, even more preferably at least 80% are removed, more preferably at least 90% are removed, more preferably at least 95% are removed, and most preferably 100% are removed. In a most preferred embodiment, in the case of a biofilter of the present invention containing a hydrolase, about 60%-100% of the pollutants or toxins are hydrolyzed in a liquid being passed through a biofilter. In a most preferred embodiment, where the AFOMC of the present invention contain an enzyme that breaks down atrazine, about 30% of the atrizine had been removed from a liquid in a time period of about 2 hours.

Additional Uses of the AFOMC of the present invention

As can be appreciated, the present invention has numerous uses across numerous fields. Advantageously, the method of using the present invention is basically similar despite the field of use. In particular, the enzyme used and method of delivery may change depending on the use, but the basic platform does not. As the uses of the invention are too numerous to enumerate herein, the scope of the invention should not be limited to the exemplary uses described herein.

Production of Biofuels

The AFOMC of the present invention may be used in the production of biofuels. It is contemplated that the MOI is any enzyme or combination of enzymes capable of hydrolyzing starch, sucrose, lactose, cellulose or hemicelluloses into fermentable sugars. These sugars can be further fermented using enzymes capable of using the sugars to produce ethanol. The AFOMC can be delivered to a biomass such as agricultural crops, such as corn, sugar cane and sugar beet, or from agricultural byproducts, such as whey and potato processing waste streams to aide in the production of ethanol.

Use of the AFOMC provides an improved production step for delivery of the desired enzymes. After the fuel and/or other are compounds produced they can be recovered by suitable processing methods depending on the particular material produced and the level of purity desired. For example, when producing ethanol the entire contents of the reaction can be transferred to a distillation unit, and 96 percent ethanol/4 percent water (by volume) can be distilled and collected. Fuel grade ethanol (99-100 percent ethanol) can be obtained by azeotropic distillation of the 96 percent ethanol, e.g., by the addition of benzene and then re-distilling the mixture, or by passing the 96 percent ethanol through molecular sieves to remove the water.

Production of Biodiesel

The AFOMC system may be used in the production of biodiesel. The conversion of vegetable oils to methyl- or other short chain esters in a single transesterification reaction using lipases has led to the production of high-grade biodiesel. It is contemplated that the AFOMC will incorporate an MOI that is a lipase. Exemplary lipases include, without limitation, lipases such as those from *Pseudomonas cepacia, Rhizomocur miehei* and *Candida antarctica*. One skilled in the art will recognize that any lipase or combination of lipases could be used as MOIs with the AFOMC in the production of biodiesel. Use of the AFOMC provides an improved production step for delivery of the lipases used in the production of an energy source.

Bioremediation

The AFOMC of the present invention can be utilized in the remediation of contaminants. The AFOMC aides in the delivery of enzymes known in the art for the reduction of contaminants. Enzymes known in the art of having the capability of breaking down or converting contaminants to less harmful substances can be used as MOIs with the AFOMC of the present invention. Suitable enzymes that may be used as MOIs, without limitation, include mono- or di-oxygenases, reductases, dehalogenases, cytochrome P450 monoxygenases, enzymes involved in lignin metabolism such as laccases, lignin- and manganese peroxidases and bacterial phophotriesteraes. Suitable enzymes also include natural occurring, synthetic, and genetically engineered enzymes. By way of example, the enzyme AtzA produced by soil bacterium *Pseudomonas* strain ADP, is capable of modifying the contaminant atrazine to the benign substance hydroatrazine (FIG. 20). By way of example the contaminated environments can include, but not limited to liquid environments, such as water, solid or semi-solid environments, such as soil, or gaseous environments, such as air. Exemplary contaminates include the following: polycyclic aromatic hydrocarbons (PAHs), polynitrated aromatic compounds, pesticides such as organochlorine insecticides, bleach-plant effluents, synthetic dyes, polymers, wood preservatives, chrysene, benzol[a]pyrene, coronene, dibenzothiophenes, cloro-dibenzofurans, cloro-dibenzo p-dioxines, atrazine, lindane, polychlorinated biphenyl, synthetic pyrethroids, carbamates, and organophosphates to name a few. Exemplary enzymes that may be used as MOIs include the following: mono- or di-oxygenases, reductases, dehalogenases, cytochrome P450 monoxygenases, enzymes involved in lignin-metabolism such as laccases, lignin and manganese peroxidases, and phosphotriesterases to name a few.

The AFOMC of the present invention may be combined with methods known in the art for remediation. Suitable methods known in the art include, without limitation, bioremediation, vacuum or air stripping, immobilization, and soil washing-flushing. Immobilization is one of the more common methods, where solid matrices are introduced into the soil that bind or otherwise minimize migration of the contaminate from the initial site. Soil washing-flushing involves the introduction of aqueous solution to the subsurface to mobilize the contaminates for treatment. It is contemplated that the AFOMC can be combined with soil-washing techniques to introduce the BEMD particles to the subsurface. Also, BEMD particles can be mixed into soil slurry and added to soil or incorporated into the desired environment through the use of soil tillage.

Fuel Cell

The AFOMC of the present invention can be utilized in fuel cells. The AFOMC aides in the delivery of enzymes known in the art for the production of an energy source. Enzymes known in the art of having the capability of breaking down organic material can be used as MOIs with the AFOMC of the present invention. AFOMCs expressing one or more of such enzymes as MOIs can be used with devices that directly convert biocatalyst power generated from the degradation of organic matter into electrical energy. Exemplary enzymes include without limitation hydrogenases, laccases and other redox enzymes that have application as electrocatalysts. In the field of biofuel cells, hydrogenases have been demonstrated that convert hydrogen to generate an electric current and possess similar energy conversion efficiency to noble-metal-based commercial methods. Laccases have also been incorporated into the design of biofuel cells since they are one of the few enzymes that can accept electrons from the cathodic compartment of a biofuel cell.

By way of example and without limitation, the AFOMC can be contacted with environments containing organic material (i.e. biomass) such as wastewater and other undesirable substrates. As the enzymes delivered by the AFOMC degrade the organic material through oxidation, hydrolysis, and other degradation methods, the fuel cell device converts this power into electricity. Fuel cell devices are known in the art such as those described in U.S. Patent Application No. 20100178530, incorporated herein by reference. Several studies on electricity production from artificial or real domestic wastewater, animal wastewater, food wastewater, and recently hydrolysate from corn stover biomass has been conducted and for this purpose several different types of fuel cells have been developed both for batch and continuous mode operations.

Biohydrogen

The AFOMC of the present invention can be utilized in the production of molecular hydrogen as a renewable, efficient and pollution-free energy source. Hydrogen is colorless, odorless, tasteless, non-toxic and, on combustion, it produces water as the only by-product. Hydrogen obtained from biomass has the potential to compete with hydrogen produced by other methods such as from natural gas, which requires the catalytic conversion of hydrocarbons or electrochemical or photochemical water splitting. Enzymes known in the art as hydrogenases can be used as MOIs with the AFOMC of the present invention. AFOMCs expressing one or more of such enzymes as MOIs can be used for the production of hydrogen, for example, by fermentation of sugar or, more preferably, from waste.

Biofilm Removal

Naturally occurring biofilms are continuously produced and often accumulate on numerous industrial surfaces and on biological surfaces. In an industrial setting, the presence of these biofilms causes a decrease in the efficiency of industrial machinery, requires increased maintenance, and presents potential health hazards. For example, the surfaces of water cooling towers become increasingly coated with microbially produced biofilm slime which both constricts water flow and reduces heat exchange capacity. Water cooling tower biofilms may also harbor pathogenic microorganisms such as *Legionella pneumophila*. Food preparation lines are routinely plagued by biofilm build-up both on the machinery and on the food product where biofilms often include potential pathogens. Industrial biofilms are complex assemblages of insoluble polysaccharide-rich biopolymers which are produced and elaborated by surface dwelling microorganisms. The chemical composition of industrial biofilms are diverse and are specific to each species of surface dwelling microorganism.

On a biological surface, the presence of these biofilms results in the growth of, and subsequent colonization by, pathogenic microorganisms on an internal or external surface of a host animal or on the surface of objects introduced into the animal (e.g. surgical implants). Animal pathogens which colonize surfaces are often maintained and protected by unique polysaccharide rich biofilms produced by the pathogen. Such biofilms coat the infected or colonized surface of the animal or implanted object and continue to be produced during the disease process. For many diseases, biofilms are required for the disease process to become established and to progress. The chemical compositions of pathogen-associated surface biofilms, which consist of complex mixtures of biopolymers, are specific to each species of pathogen.

The AFOMC can be utilized to treat and remove biofilms. Enzymes known in the art as hydrolytic enzymes can be used as MOIs with the AFOMC of the present invention. AFOMCs expressing one or more of such enzymes as MOIs can be delivered to biofilm environments such that the hydrolytic enzymes significantly degrade or remove the biofilm. Techniques are known in the art for biofilm removal such as those described in U.S. Patent Application No. 20100159563, incorporated herein by reference.

Drug Delivery

The AFOMC of the present invention may be utilized in delivering therapeutic molecules to a subject. Molecules such as therapeutic proteins may be used as MOIs with the AFOMC. These bioparticles may be administered to a subject by methods known in the industry or described herein. Suitable therapeutic proteins include those known in the art and those yet to be discovered.

Unless defined otherwise, all technical and scientific terms used herein have the same meaning as is commonly understood by one of skill in the art to which this invention belongs at the time of filing.

EXAMPLES

Example 1

This example illustrates synthesis and functionalization of ordered mesoporus carbon Materials and Methods.

The mesoporous silica template (SBA-15) and ordered mesoporous carbon (OMC) were synthesized with the procedures described by Gu et al. (Gu, 2007). The SBA-15 template for the synthesis of OMC consists of uniform array of carbon rods arranged in hexagonal pattern (Hartmann, 2005). Synthesized OMC subsequently was treated with nitric acid, subsequently chlorinated with thionyl chloride ($SOCl_2$), then functionalized with ethylenediamine (EDA) (Gu, 2007; Tamai, 2006b; Zhu, 2011). Two and half grams of OMC were treated with 25 mL of 4M nitric acid ($HNO_3$) at 50'C for 2 hours. The $HNO_3$-treated activated carbon was chlorinated with 5% thionyl chloride ($SOCl_2$) in 20 mL of toluene solution at 70'C for 6 hrs. The immobilization of diamine on OMC was achieved by treating the chlorinated OMC with 0.05-Methylenediamine dissolved in 40 mL in toluene for 4 hours. The functionalized OMC was collected by filtration and washed by toluene for 2 hours to remove free EDA from carbon. The resulting functionalized ordered mesoporous carbon was oven-dried overnight at 40'C under vacuum (Yantasee et al., 2004).

Enzyme Production and Purification

Total chromosomal DNA was isolated from an overnight culture of Pseudomonas sp. strain ADP grown in R media as described in Thompson et al. 2010. DNA was measured spectrophotometrically and utilized as template DNA for PCR amplification of the atzA gene.

A) The Purification of Recombinant Protein

PCR primers were designed for atzA open reading frame with promoter region at the upstream. The amplicons with correct gene size were cloned into the cloning vector pSC-A (Stratagene) and correct clones screened via restriction enzyme digestion, agarose electrophoresis and DNA sequencing analysis.

A 5-ml overnight culture of E. coli containing pSC-AtzA was used to inoculated 1 L of LB with ampicillin 100 µg/ml for protein expression. The culture preparation was incubated at 37'C with shaking and monitored until OD600 reached 0.8. The culture for protein expression was harvested by centrifugation at 5000 rpm for 20 min and the cell pellets were collected. The cell pellets were re-suspended with the solution of 25 mM MOPS, pH6.9, and bead-beaten for 2 min at maximum speed at 4'C. The supernatant was collected as crude extract, after the bead-beaten preparation was microcentrifuged at maximum speed for 90 min at 4'C. The ammonium sulfate precipitation was performed with the crude extract for 20% saturation. The precipitation preparation was centrifuged and the pellets were collected and re-suspended with the solution of 25 mM MOPS, pH6.9. The re-suspension was dialyzed against the solution of 25 mM MOPS, pH6.9 at 4'C to eliminate the remaining ammonium sulfate. The purity of the AtzA protein was determined by SDS-PAGE and Coomassie Blue staining procedure as 40% at this point. The protein concentration of the protein preparation was determined by NanoDrop ND-1000 spectrophotometer.

B) The Construction and Expression of Recombinant Protein with His Tag for Purification PCR primers were created that contained both a 5' overhang and 3' overhang bearing part of the T7 promoter elements with a N-terminal 6xHis Tag and T7 terminator regions, respectively. The amplicon was then subjected to PCR purification with a PCR purification kit (Qiagen), and used as template DNA for a second PCR reaction which annealed the remainder of the T7 promoter elements and T7 terminator. PCR primers utilized are described in Table 1. Correct amplicons were cloned into the cloning vector pSC-A (Stratagene) and correct clones screened via restriction enzyme digestion and DNA sequencing at the University of Missouri DNA core.

1 hour to allow for the transcription/translation reaction to occur. The reaction was stopped on ice for 1 minute. The total protein was then mixed 1:1 in 2×His column Binding buffer (Zymo Research). After mixing, the protein mixture was purified via the H is purification kit (Zymo Research) as per the manufacturers suggestion. The purified protein was subjected to dialysis overnight against 25 mM MOPS buffer, pH6.9 with one change of buffer. The resultant protein pool (pure AtzA) was analyzed via a NanoDrop ND-1000 spectrophotometer for protein concentration. Protein purity was determined via separation of 50 µg of AtzA protein on a 4-12% Tris-Glycine precast gel (Bio-rad) subjected to Coomassie blue staining analysis. The protein purity was determined to be >95% AtzA for all reactions. The purified AtzA was used immediately or stored at −20° C. until needed.

Figure 2:
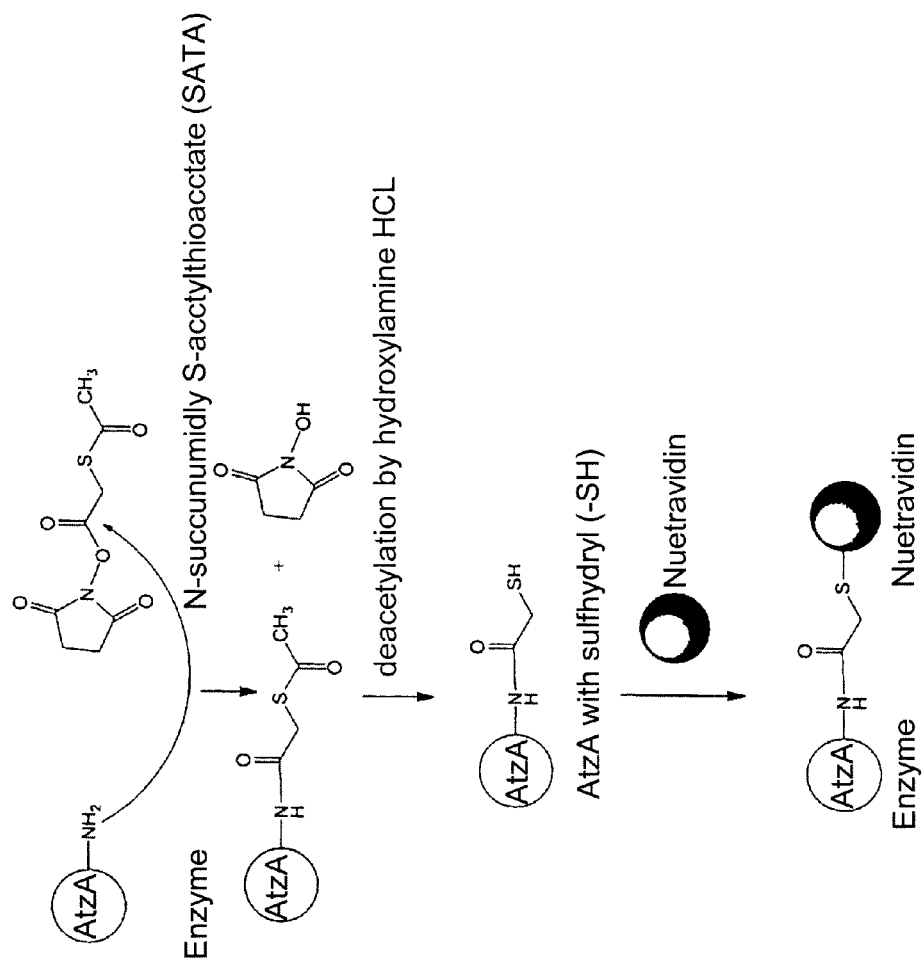
FIG. 2. Conjugation of enzyme AtzA to nuetravidin.

Conjugation and Immobilization of Enzymes on the Functionalized Ordered Mesoporous Carbon Purified AtzA or β-galactosidase (Thermo-Pierce) was diluted in MOPS or PBS, respectively, to a concentration of 5 µg/µl. N-succunumidly S-acetylthioacetate (SATA) solution was prepared by mixing 2 mg of N-succunumidly S-acetylthioacetate (SATA) in 200 µl of dimethylformamide (DMF). Twenty µl of the SATA solution was added to 1 ml of target protein prep to conjugate the SATA groups onto the free amine groups of the AtzA/β-galactosidase enzymes. This reaction occurred for 30 minutes at room temperature. As shown in FIG. 1, the SATA-conjugated amine groups of AtzA/β-galactosidase were then reduced (deacetylated) by reacting with hydroxylamine HCL in Maleimide Conjugation Buffer (Thermo-Pierce). After 2 hours of chemical reduction, the protein preparations (5 mg/ml) were separated from the free SATA groups and hydroxylamine via desalting columns (Thermo-Pierce). The nuetravidinated purified enzymes AtzA was accomplished by mixing 1 ml of Nuetravidin in Maleimide Conjugation Buffer (Thermo-Pierce, 5 mg/ml) in equal volume of the reduced SATA-modified enzymes incubated overnight at 4'C (FIG. 2). Centricon centrifugation filters (3,000 MWCO) were utilized to exchange the enzymes into MOPS or PBS buffer for AtzA or (3-galactosidase, respectively.

Figure 3:
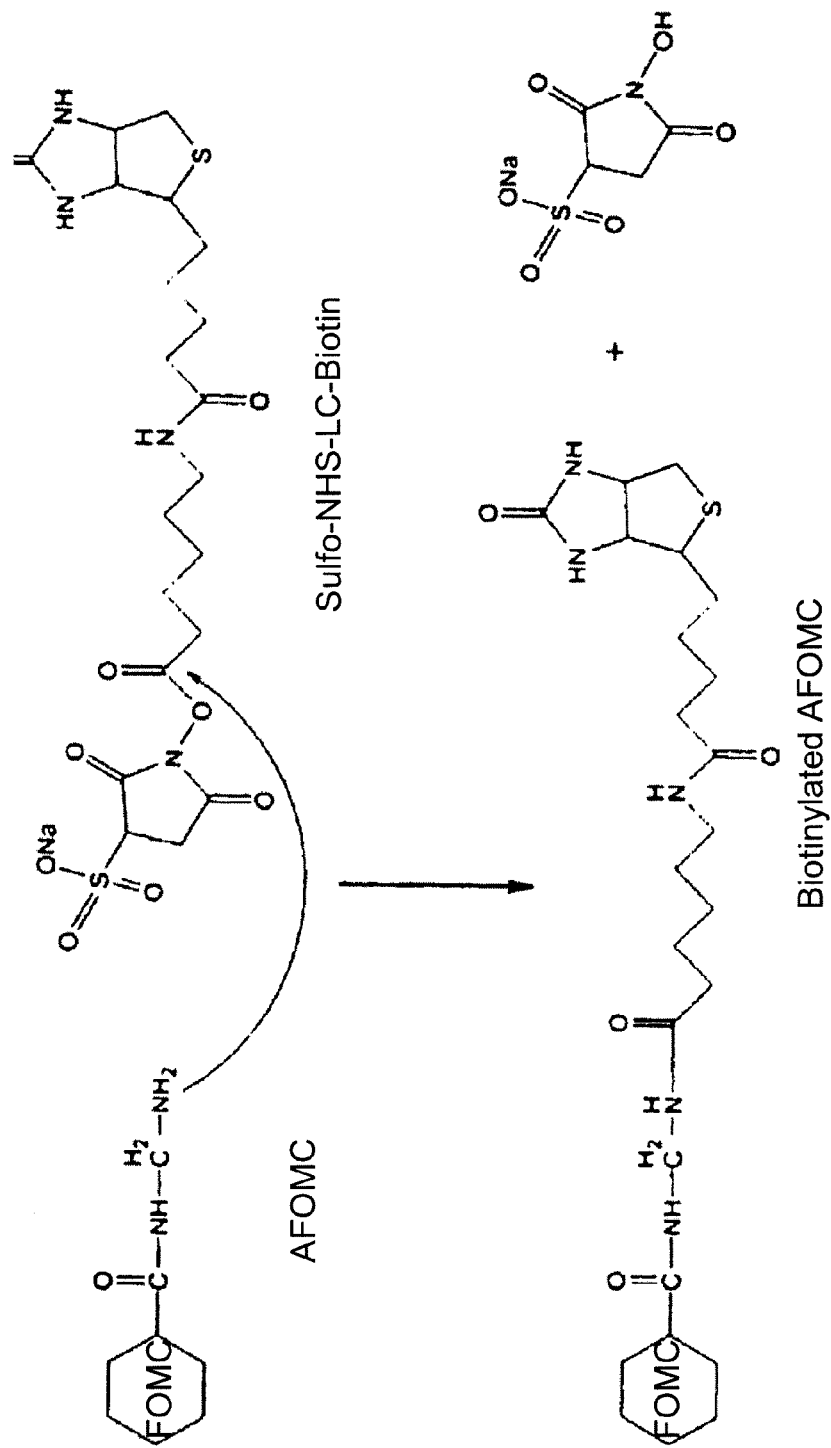
FIG. 3. Biotinylation of amide-functionalized ordered mesoporous carbon (AFOMC).
Figure 4:
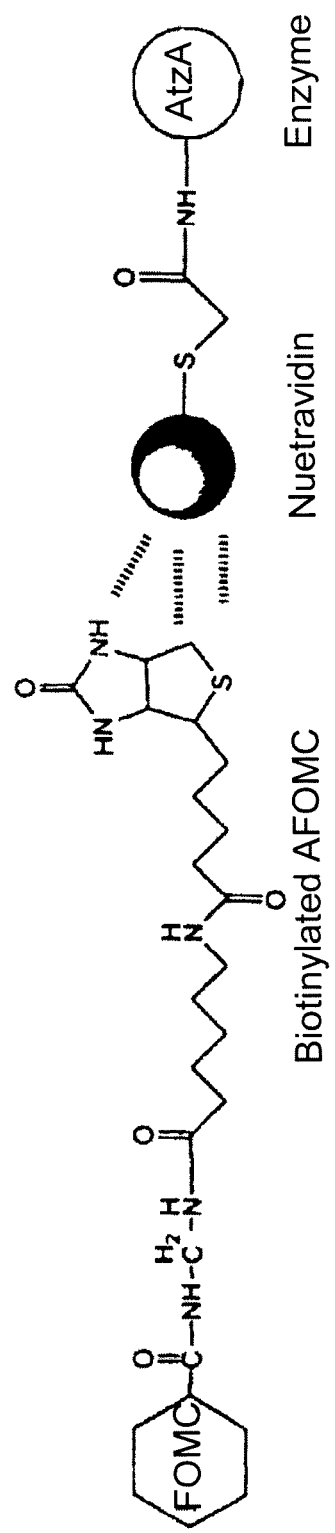
FIG. 4. Conjugation of biotinylated functionalized ordered mesoporous carbon (FOMC) to nuetravidinated purified enzymes AtzA.

Amide-functionalized ordered mesoporous carbon (AFOMC, 5 mg/ml) was conjugated via its exposing amine groups to biotin using the EZ-Link Sulfo-NHS-LC kit (Thermo-Pierce) (FIG. 3). The nuetravidinated purified enzymes were then added to the biotinylated AFOMC in the ratio of 1:5 to allow the nuetravidin-biotin binding occurred (FIG. 4).

TABLE 1

PCR Primers.

| | | |
|---|---|---|
| Without 6xHis | 5' AtzA | aggaggtagatacatgcaaacactcagcatccag |
| | 3' AtzA | ggggttatgctatcactattattactagaggctgcgccaagctgg |
| | T7 Promoter | atattatacgactcactatagggagataaggaggtagatac |
| | T7 Terminator | atatcaaaaaaccctcaagacccgtttagaggccccaaggggttatgct |
| With 6xHis | 5' His AtzA | aggaggtagatacatgcatcaccatcaccatcaccaaacgctcagcatcc |
| | 3' AtzA | ggggttatgctatcactattattactagaggctgcgccaagctgg |
| | T7 Promoter | atattaatacgactcactatgggagataaggaggtagatac |
| | T7 Terminator | atatcaaaaaaccctcaagaccgtttagaggccccaaggggttatgct |

AtzA protein expression was initiated using an in vitro T7 S30 TNT (transcription and translation) protein expression system (Promega). Briefly, 1 µg of atzA plasmid DNA was mixed with kit components as per the manufacturer's recommendations. The reaction mixture was incubated at 37° C. for Chemical Analysis One hundred microliters of atrazine solution with mixture of $^{14}C$-labeled atrazine and non-labeled atrazine was applied into 1 mL of buffers containing 10 mM KCl in 25 mM (MOPS) buffer (pH 6.9) to achieved the total atrazine concentration of 2000 ppb (μg/L) with radioactivity 0.1 μci/mL. One hundred microlilters of AFOMC conjugated with AtzA enzymes (5 mg/ml) was added into the buffer solution containing atrazine and incubated at room temperature 25° C. The samples were injected into a Shimadzu SCL-10Avp high performance liquid chromatography system (HPLC) (Columbia, Md.). $^{14}$C-ATR and its degradation products were separated using a silica-based Columbus C8 column (4.6 mm×250 mm, 5 μm; Phenomenex, Torrance, Calif.). The radioactivity was detected by an in-line IN/US ScinFlow β-Ram Model 3 (Tampa, Fla.) flow scintillation analyzer (HPLC-FSA). Injection volume was 10 μL, and mobile phase flow rate was 1 mL min-1. The $^{14}$C-ATR and its metabolites were eluted with a two-part mobile phase gradient. Mobile phase A consisted of 0.1% $H_3PO_4$ buffer (pH=2.1), and mobile phase B was 100% ACN. The gradient started at 10% and ramped linearly to 40% at 30 min, 75% at 40 min, 10% at 45 min, and held at 10% for 14 min. Metabolites were identified by comparing the retention times of unlabeled standards based on HPLC-UV detection at 220 nm. The standards including atrazine (ATR), deethylatrazine (DEA), deisopropylatrazine (DIA), hydroxyatrazine (HA), deisopropylhydroxyatrazine (DIHA), deethylhydroxyatrazine (DEHA), didealkylatrazine (DDA), ammeline (AM) and Ammelide were purchased through ChemService (West Chester, Pa.).

To determine the β-galactosidase activity, the ortho-Nitrophenyl-β-galactoside (ONPG) was used as subtract. The concentrations of free ortho-nitrophenol as a result of the hydrolyzed ortho-Nitrophenyl-β-galactoside were measured spectrophotometrically at 420 nm wavelength.

Results and Discussion

Figure 5A:
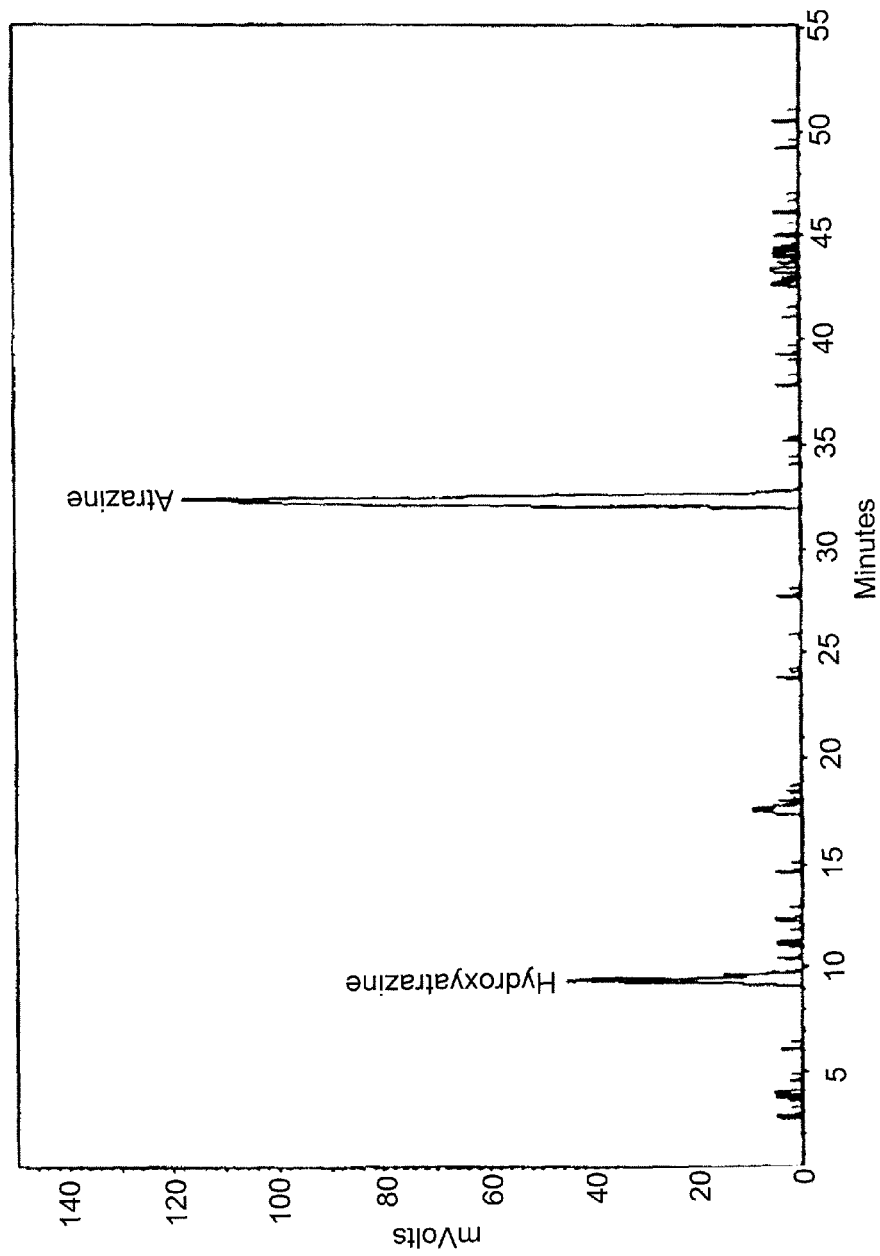
FIG. 5. Radiochromatograms of $^{14}C$ labeled atrazine reacted with amide-functionalized ordered mesoporous carbon conjugated with AtzA chlorohydrolase (A), and $^{14}C$ labeled atrazine in control (reacted with DI water) for 2 hours (B).
Figure 5B:
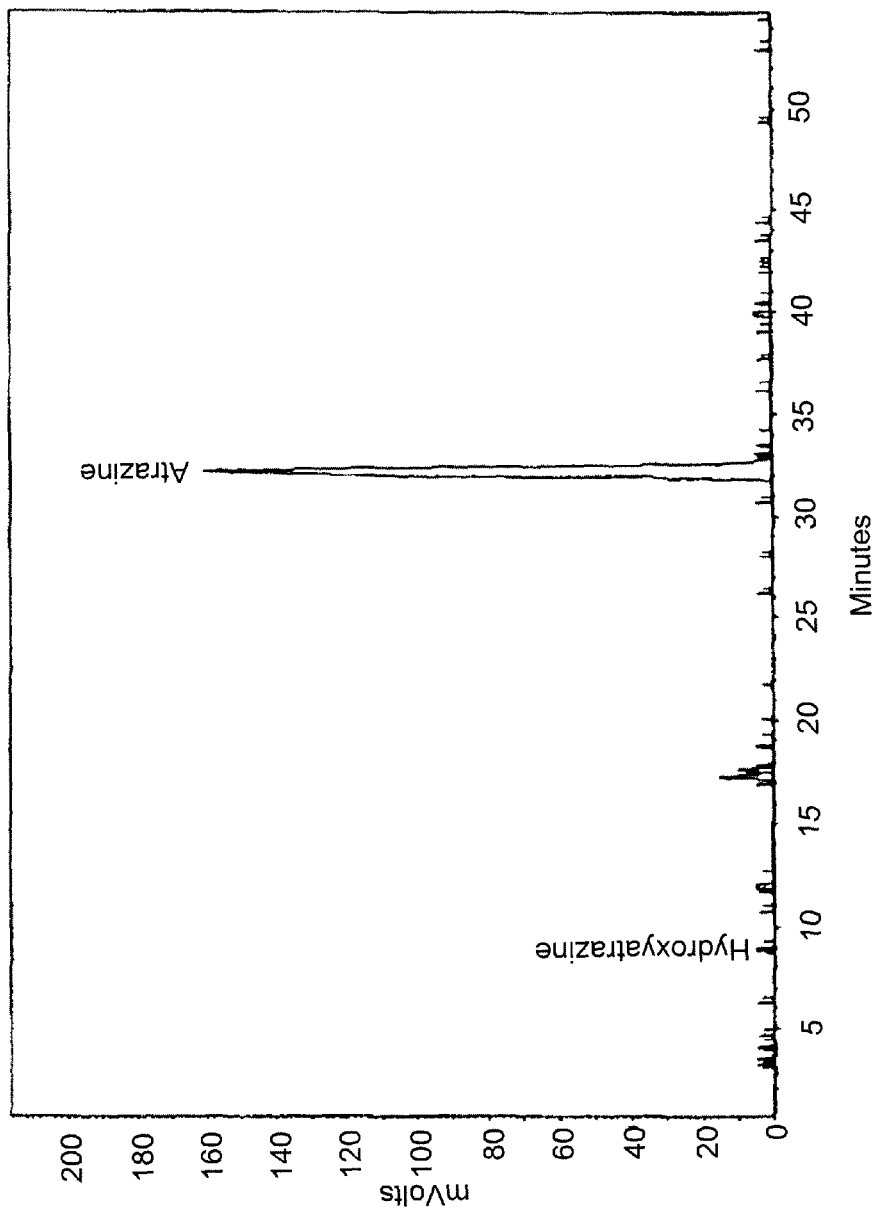

N-Hydroxysulfosuccinimide (Sulfo-NHS) ester of biotin was used for conjugate the NHS-activated biotin with the FOMC. The primary amine as results of the amide functionalization reaction reacts efficiently with the NHS-activated biotin (FIG. 2). As shown in FIG. 5, the chlorohydrolaseAtzA immobilized on the surface of functionalized ordered mesoporous carbon still retained it enzymatic activity. It transformed about 30% of atrazine in the solution into less toxic and less mobile hydroxyatrazine within 2 hours. On the other hand, the concentration of atrazine in the control treatment was constant in the solution throughout the experimental period. It should be noted that, the half-life of atrazine is about 350 days under the sterilized condition in this studies. Therefore, we did not expect to observe any degradation of atrazine in the control treatment.

Figure 6A:
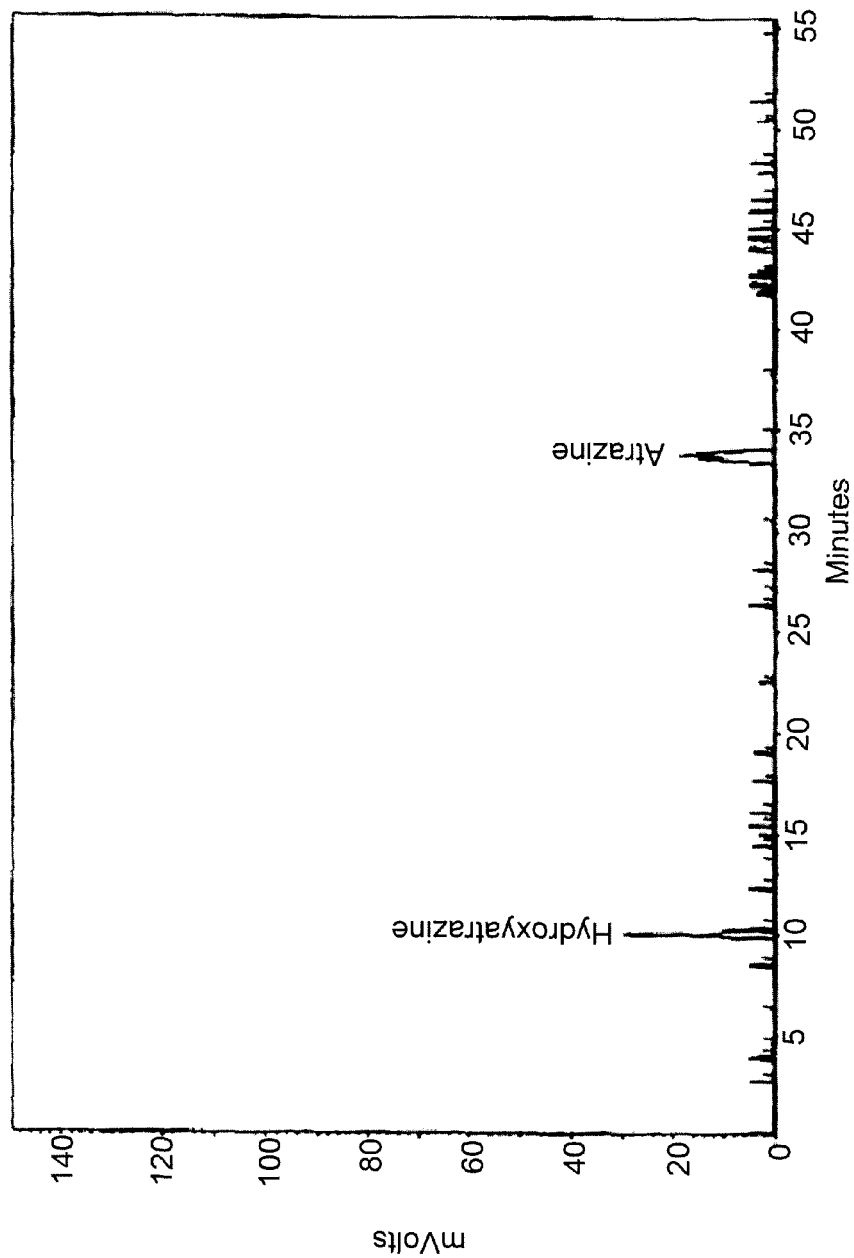
FIG. 6. Radiochromatograms of $^{14}C$ labeled atrazine reacted with amide-functionalized ordered mesoporous carbon conjugated with AtzA chlorohydrolase (A), and $^{14}C$ labeled atrazine in control (reacted with DI water) for 14 days (B).
Figure 6B:
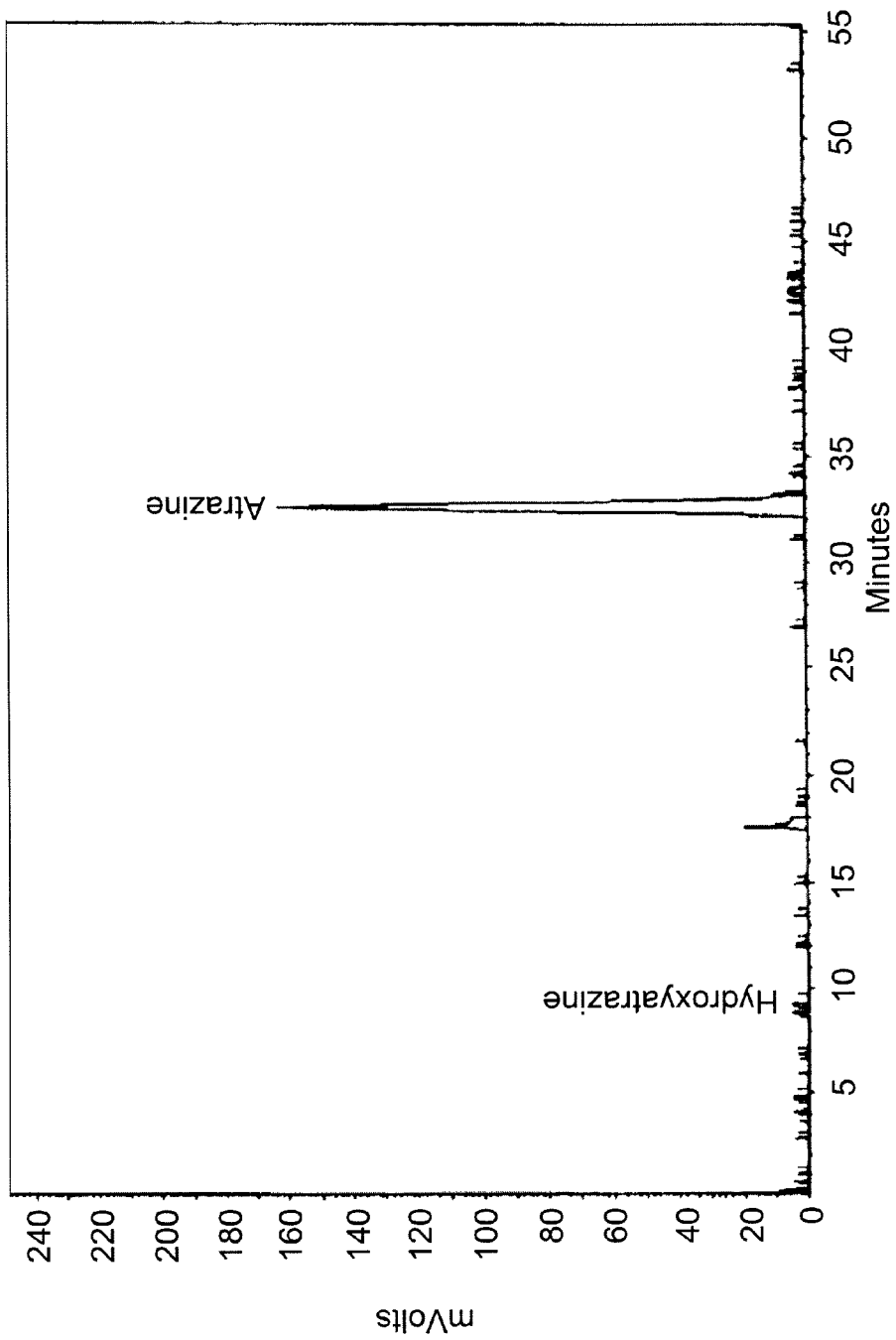

The decreased in total radioactivity in the solution over time as shown in FIG. 6 suggested the high specific surface area of the AFOMC provide a large adsorption capacities for substrate atrazine and its metabolite hydroxyatrazine through electrostatic interactions and/or covalent bindings. The AFOMC naturally draws in charged molecules, such as the herbicide atrazine, towards the attached enzymes that will convert the atrazine to benign hydroxyatrazine. This system can be used with a variety of enzymes and pollutants. We have utilized this invention to design a biofilter that removes atrazine from stagnant and free flowing water sources and have proven the concept in small scale laboratory experiments. In addition, immobilization of multiple ATR-degrading enzymes, such as combination of AtzA, AtzB, AtzC, AtzD, AtzE, and AtzF, may accelerate the degradation and transformation processes.

Figure 7:
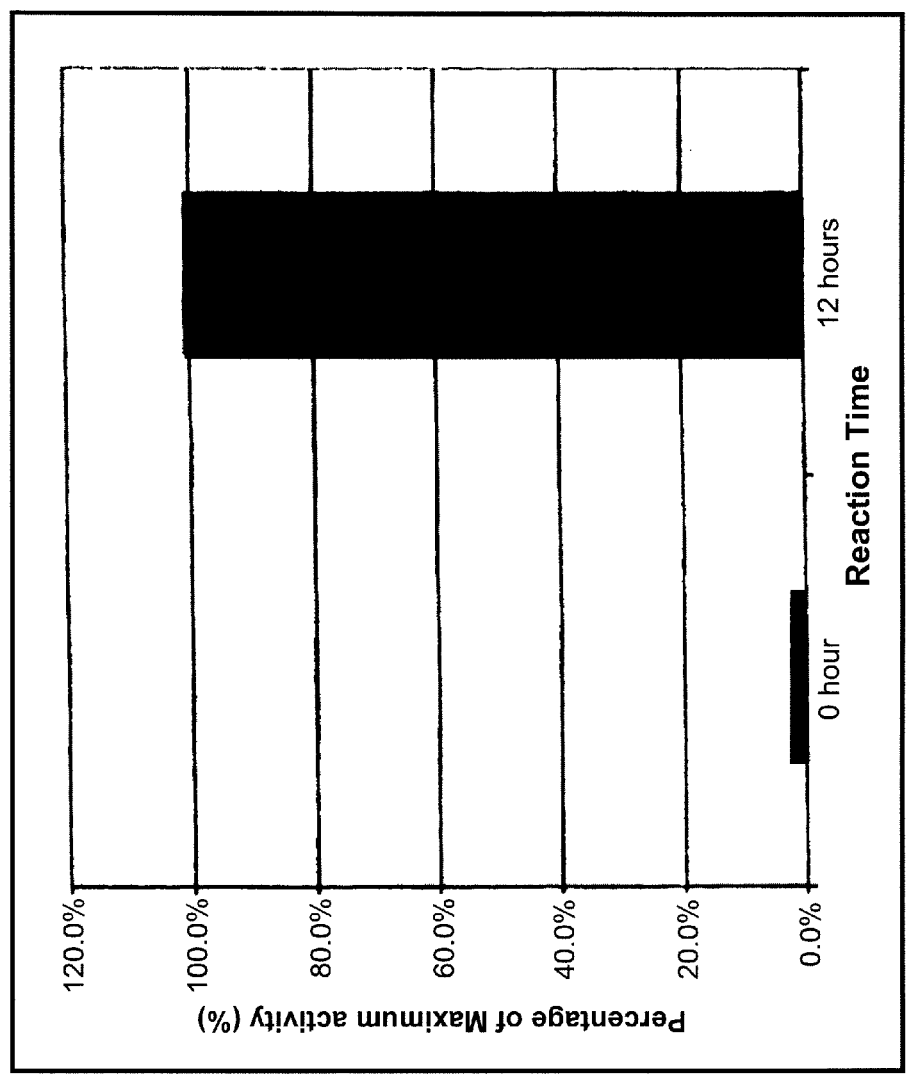
FIG. 7. Hydrolytic conversion of ortho-nitrophenyl-β-galactoside (ONPG) by 10 mg of amide-functionalized ordered mesoporous carbon (AFOMC) immobilized with β-galactosidase in 200 ml of 1M ONPG solution.
Figure 8:
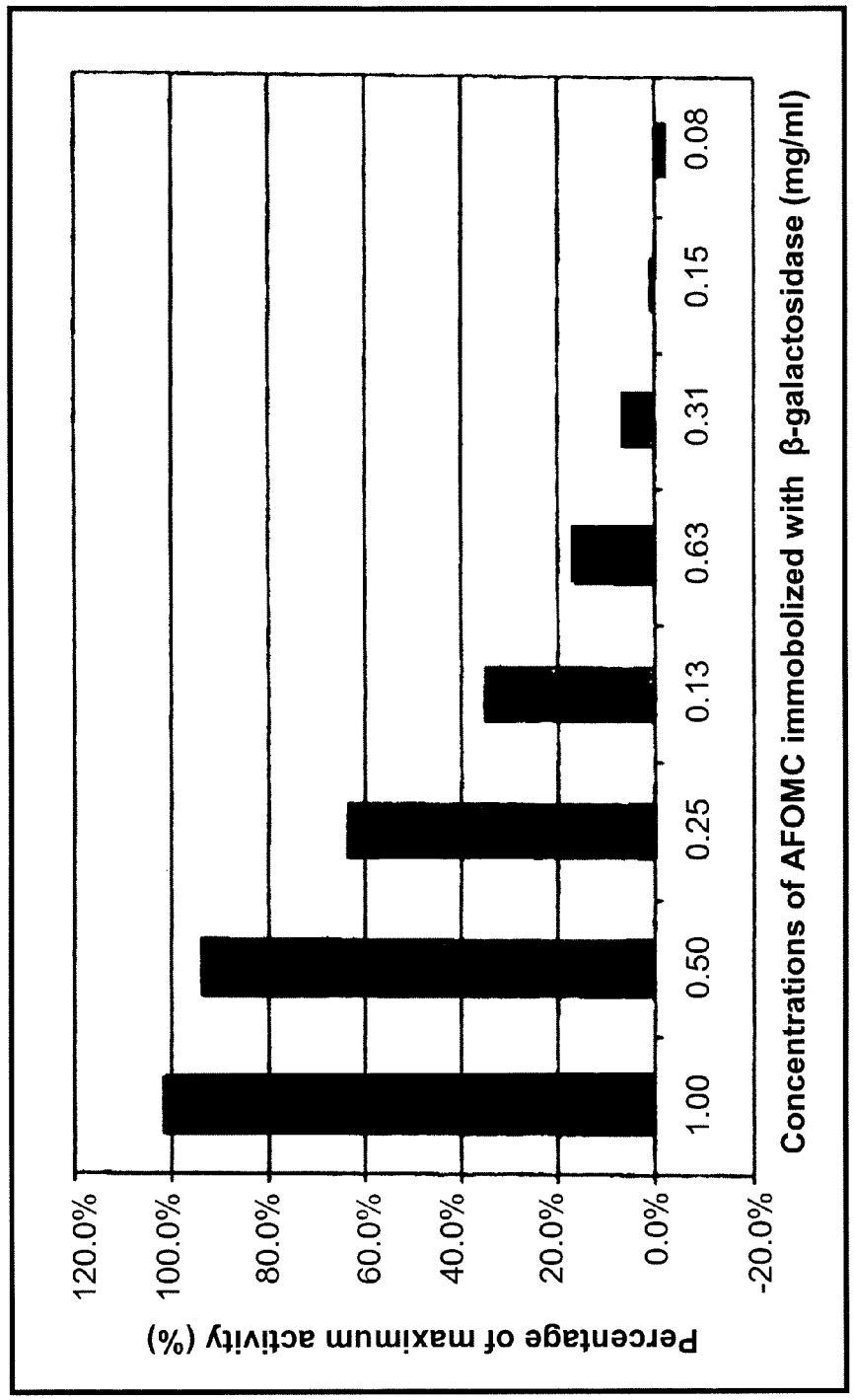
FIG. 8. Hydrolytic conversion of ortho-nitrophenyl-β-galactoside (ONPG) by amide-functionalized ordered mesoporous carbon (AFOMC) immobilized with β-galactosidase as a function of concentrations of AFOMC-based biocatalyst.

This system can be used with a variety of enzymes to mitigate the contamination of both organic and inorganic pollutants. As shown in the FIG. 7, more than 95% of the ortho-nitrophenyl-β-galactoside (ONPG) was hydrolyzed by the AFOMC immobilized with β-galactosidase during 12 hours of reaction period. As we expected, the hydrolysis of ONPG by amide-functionalized ordered mesoporous carbon (AFOMC) immobilized with β-galactosidase was significantly ($p<0.005$) enhanced with the increasing concentrations of AFOMC-based biocatalyst (FIG. 8).

Figure 9A:
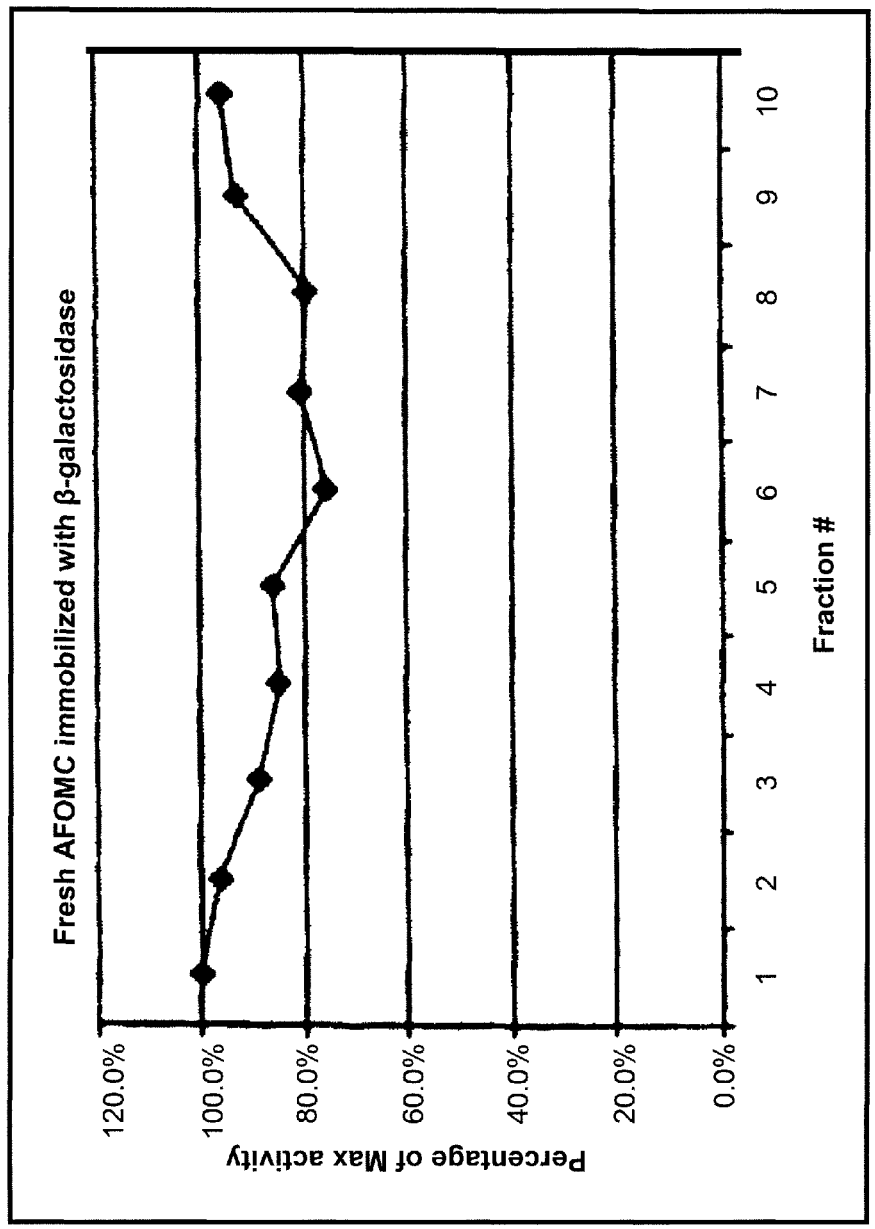
FIG. 9. Hydrolytic conversion of ortho-nitrophenyl-β-galactoside (ONPG) by the flow-through column packed with freshly prepared (A) and 6-week old (B) amide-functionalized ordered mesoporous carbon (AFOMC) immobilized with β-galactosidase. The eluate was collected into each fraction.
Figure 9B:
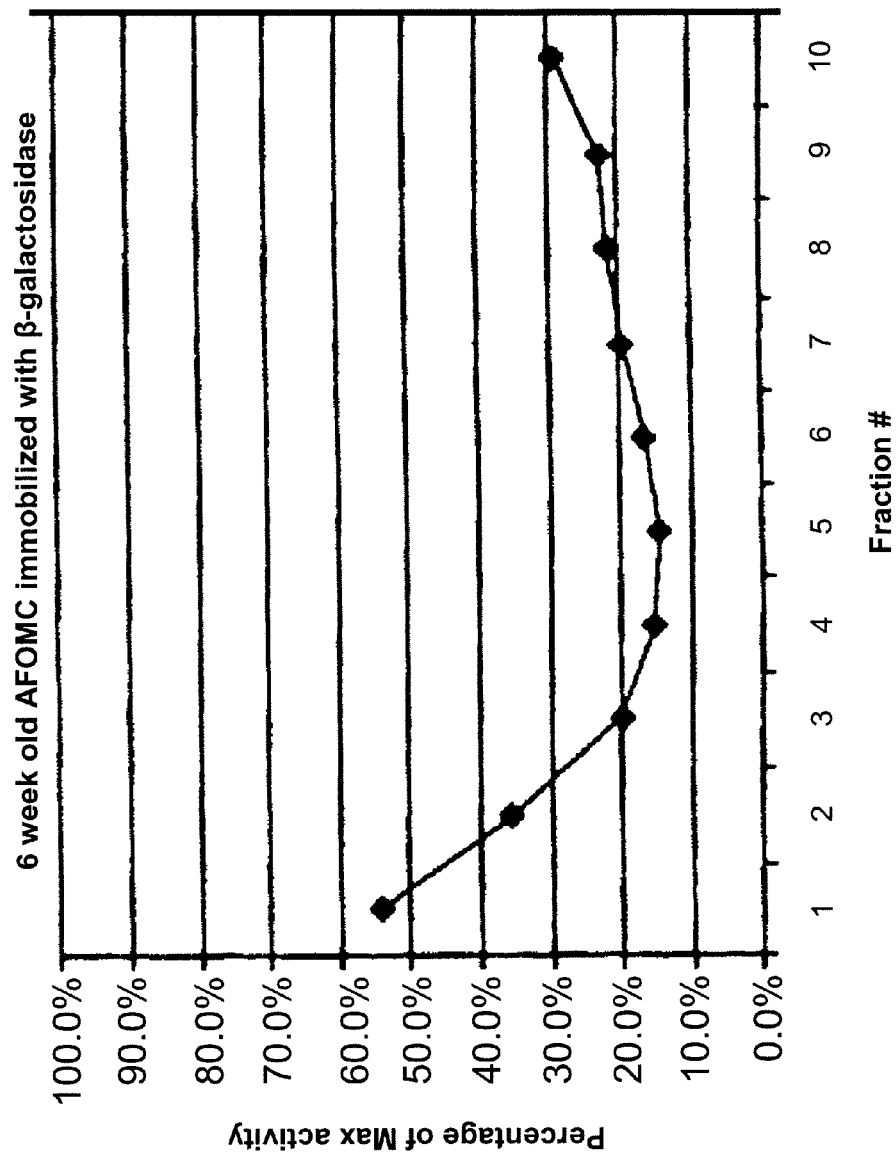

We have utilized this invention to design a biofilter that removes atrazine and other class of pollutants from stagnant and free flowing water sources and have proven the concept in small scale laboratory experiments. As the results shown in FIG. 9A, when the substrate nitrophenyl-β-galactoside ONPG passed through the flow-through column packed with AFOMC immobilized with β-galactosidase, 80% to 100% of the ONPG in the effluent was rapidly hydrolyzed. The results also suggested that the column packed with freshly prepared AFOMC-based biocatalysts outperformed the system packed with 6-weeks old AFOMC-based biocatalysts (FIG. 9B).

Other Possible Uses

This conjugation of bioactive enzymes onto the amide-functionalized ordered mesoporous carbon have a wide range of other commercial applications for development biocatalysts, biofilters (e.g., Xp1A cytochrome P450 for removing RDX, PnrA for removing TNT, DbfB dioxin dioxenase for removing dioxin, ChrR chromium reductase for reducing chromium 6+ to chromium 3+), fuel cell (enzyme based biological fuel cell), imaging (antibodies and fluorescent proteins), biofuel production, drug delivery systems (e.g., antimicrobial proteins: lysozyme etc), medical therapeutics and biosensors.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein.

REFERENCES

Boundy-Mills, K. L., M. L. De Souza, R. T. Mandelbaum, L. P. Wackett, and M. J. Sadowsky. 1997. The atzB gene of *Pseudomonas* sp. strain ADP encodes the second enzyme of a novel atrazine degradation pathway. Appl. Environ. Microbiol. 63:916-23.

Contescu, A., Contescu, C. Putyera K. and Schwarz, J. A. 1998. Acid buffering capacity of basic carbons revealed by their continuous pK distribution Carbon 36 247-258.

De Souza, M. L., M. J. Sadowsky, and L. P. Wackett. 1996. Atrazine chlorohydrolase from *Pseudomonas* sp. strain ADP: Gene sequence, enzyme purification, and protein characterization. J. Bacteriol. 178:4894-4900.

De Souza, M. L., L. P. Wackett, and M. J. Sadowsky. 1998a. TheatzABC genes encoding atrazine catabolism are located on a self-transmissible plasmid in *Pseudomonas* sp. strain ADP. Appl. Environ. Microbiol. 64: 2323-2326.

De Souza, M. L., J. Seffernick, B. Martinez, M. J. Sadowsky, and L. P. W. 1998. 1998b. The atrazine catabolism genes atzABC are widespread and highly conserved. J. Bacteriol. 180:1951-1954.

Garciá-González, V., F. Govantes, L. J. Shaw, R. G. Bums, and E. Santero. 2003. Nitrogen Control of Atrazine Utilization in *Pseudomonas* sp. Strain ADP Appl. Environ. Microbiol. 69:6987-6993.

Gilliom, R. J., J. E. Barbash, C. G. Crawford, P. A. Hamilton, J. D. Martin, N. Nakagaki, L. H. Nowell, J. C. Scott, P. E. Stackelberg, G. P. Thelin, and D. M. Wolock. 2006. The Quality of Our Nation's Waters: Pesticides in the Nation's Streams and Ground Water: Pesticides in the Nation's Streams and Ground Water, 1992-2001. U.S. Department of the Interior, U.S. Geological Survey Reston, Va.

Gu, Z. M., Deng, B, John Yang. 2007. Synthesis and evaluation of iron-containing ordered mesoporous carbon (FeOMC) for arsenic adsorption. Microporous and Mesoporous Materials 102:265-273.

Hartmann, M. 2005. Ordered mesoporous materials for bioadsorption and biocatalysis. Chem. Mater. 17:4577-4593.

Hayes, T. B., P. Case, S. Chui, D. Chung, C. Haeffele, K. Haston, M. L. V. P. Mai, Y. Marjuoa, J. Parker, and M. Tsui. 2006. Pesticide Mixtures, Endocrine Disruption, and Amphibian Declines: Are We Underestimating the Impact? Environ. Health Perspect. 114:40-50.

Jarrais, B., Silva A. R. and Freire, C. 2005. Anchoring of VanadylAcetylacetonate onto Amine-Functionalised Activated Carbons: Catalytic Activity in the Epoxidation of an Allylic Alcohol Eur. J. Inorg. Chem.: 4582-4589

Lin, C. H., R. N. Lerch, R. J. Kremer, H. E. Garrett, R. P. Udawatta, and M. F. George. 2005. Soil microbiological activities in vegetative buffer strips and their association with herbicides degradation., p. 1-10, In K. N. Brooks and P. F. Folliott, eds. Moving Agroforestry into The Mainstream: Proceedings of the Ninth Conference on Agroforestry in North America, 12-15 Jun. 2005. Department of Forest Resources, University of Minnesota, St. Paul, Minn.

Mandelbaum, R. T., D. L. Allan, and L. P. Wackett. 1995. Isolation and characterization of a *Pseudomonas* sp. that mineralizes the s-triazine herbicide atrazine. Appl. Environ. Microbiol. 61:1451-1457.

Martinez, B., J. Tomkins, L. P. Wackett, R. Wing, and M. J. Sadowsky. 2001. Complete Nucleotide Sequence and Organization of the Atrazine Catabolic Plasmid pADP-1 from *Pseudomonas* sp. Strain ADP. J. Bacteriol. 183:5684-5697.

Puri, B. R., and Hazra, R. S. 1971. sulfur surface complexes on charcoal Carbon 9:123.

Sadowsky, M. J., Z. Tong, M. De Souza, and L. P. Wackett. 1998. AtzC is a new member of amidohydrolase protein superfamily and is homologous to other atrazine metabolizing enzyme. J. Bacteriol. 180:152-158.

Tamai, H., Shiraki, K. Shiono T. and Yasuda, H. 2006a. Surface functionalization of mesoporous and microporous activated carbons by immobilization of diamine. J. Colloid Interface Sci 295(1):299-302.

Tamai, H., Shiraki, K., Yasuda, H. 2006b. Surface functionalization of mesoporous and microporous activated carbons by immobilization of diamine. J. Colloid and Interface Sci. 295:299-302.

Thompson, B. M., Lin, C.-H., Hsin-Yeh Hsieh, Kremer, R. J., Lerch, R. N. Garrett, H. E. 2010. *J Environ Qual*, 2010, 39, 1999-2005.

United States Department of Agriculture. 2004. Agricultural Chemical Usage, 2003 Field Crops Summary. Report Ag Ch1 (04) a. National Agricultural Statistics Service. Washington, D.C.

Waller, S. A., K. Paul, S. E. Peterson, and J. E. Hitti. 2010. Agricultural-related chemical exposures, season of conception, and risk of gastroschisis in Washington State. American Journal of Obstetrics & Gynecology 202: 241.e1-241.e6.

Yantasee, W., Y. H. Lin, and G. E. Fryxell. 2004. Selective Removal of Copper (II) from Aqueous Solutions Using Fine-Grained Activated Carbon Functionalized with Amine. Ind. Eng. Chem. Res. 43:2759-2764.

Zhu, J. 2011. Adsorption of aqueous mercury by amide-functionalized ordered mesoporous carbon absorbent unpublished.

The invention claimed is:

1. A contaminate reduction composition comprising:
   a) an amide-functionalized ordered mesoporous carbon (AFMOC); conjugated with
   b) a biotin conjugate; and,
   c) a toxin-degrading enzyme.

2. The contaminate reduction composition of claim 1, wherein the toxin-degrading enzyme degrades atrazine.

3. The contaminate reduction composition of claim 1, wherein the biotin conjugate is chemically associated with the amide-functionalized ordered mesoporous carbon.

4. The contaminate reduction composition of claim 1, wherein the toxin-degrading enzyme is capable of binding to the biotin conjugate.

* * * * *